(12) United States Patent
Wetzel et al.

(10) Patent No.: US 11,925,707 B2
(45) Date of Patent: Mar. 12, 2024

(54) CO-PROCESSED LUBRICANT:MCG FOR TABLETS

(71) Applicant: JRS Pharma Gmbh & Co. KG, Rosenberg (DE)

(72) Inventors: Sabine Wetzel, Rosenberg (DE); Tobias Goetz, Rosenberg (DE); Gernot Warnke, Rosenberg (DE)

(73) Assignee: JRS Pharma GMBH & CO. KG (DE)

( * ) Notice: Subject to any disclaimer, the term of this patent is extended or adjusted under 35 U.S.C. 154(b) by 279 days.

(21) Appl. No.: 17/201,142

(22) Filed: Mar. 15, 2021

(65) Prior Publication Data

US 2022/0287974 A1    Sep. 15, 2022

(51) Int. Cl.
*A61K 9/16* (2006.01)
*A61K 9/10* (2006.01)
*A61K 9/20* (2006.01)

(52) U.S. Cl.
CPC .............. *A61K 9/1652* (2013.01); *A61K 9/10* (2013.01); *A61K 9/1617* (2013.01); *A61K 9/2013* (2013.01); *A61K 9/2054* (2013.01)

(58) Field of Classification Search
CPC ...... A61K 9/16; A61K 9/1605; A61K 9/1682; A61K 9/1652
See application file for complete search history.

(56) References Cited

U.S. PATENT DOCUMENTS

| | | | |
|---|---|---|---|
| 3,141,875 A | 7/1964 | Battista et al. | |
| 5,585,115 A | 12/1996 | Sherwood et al. | |
| 5,725,883 A | 3/1998 | Staniforth et al. | |
| 5,725,884 A | 3/1998 | Sherwood et al. | |
| 5,741,524 A | 4/1998 | Staniforth et al. | |
| 5,858,412 A | 1/1999 | Staniforth et al. | |
| 5,866,166 A | 2/1999 | Staniforth et al. | |
| 5,948,438 A | 9/1999 | Staniforth et al. | |
| 6,103,219 A | 8/2000 | Sherwood et al. | |
| 6,106,865 A | 8/2000 | Staniforth et al. | |
| 6,217,909 B1 | 4/2001 | Sherwood et al. | |
| 6,358,533 B2 | 4/2002 | Sherwood et al. | |
| 6,395,303 B1 | 5/2002 | Staniforth et al. | |
| 6,471,994 B1 | 10/2002 | Staniforth et al. | |
| 6,521,261 B2 | 2/2003 | Sherwood et al. | |
| 6,746,693 B2 | 6/2004 | Staniforth et al. | |
| 6,858,231 B2 | 2/2005 | Sheerwood et al. | |
| 6,866,867 B2 | 3/2005 | Staniforth et al. | |
| 6,936,277 B2 | 8/2005 | Staniforth et al. | |
| 7,879,382 B2 | 2/2011 | Tuason et al. | |
| 9,055,757 B2 | 6/2015 | Tan et al. | |
| 2005/0147673 A1* | 7/2005 | Staniforth | A61K 9/2054 264/109 |
| 2014/0212563 A1 | 7/2014 | Bache et al. | |

* cited by examiner

*Primary Examiner* — Micah Paul Young
(74) *Attorney, Agent, or Firm* — Davidson, Davidson & Kappel, LLC

(57) ABSTRACT

The present invention is directed to a co-processed lubricant excipient which can be used to manufacture tablets, and pharmaceutical compositions containing the same.

23 Claims, 4 Drawing Sheets

CO-PROCESSED LUBRICANT:MCG FOR TABLETS

FIELD OF THE INVENTION

The present invention is related to a novel excipient for use in the manufacture of, e.g. pharmaceuticals and nutraceuticals, and in particular, solid dosage forms such as tablets.

BACKGROUND OF THE INVENTION

The present invention relates to a novel excipient for use in the manufacture of solid dosage forms such as tablets, including tablets consisting of excipients and tablets comprising excipients and one or more active ingredients. The final product may be, e.g., a pharmaceutical and/or a nutraceutical.

In order to prepare a solid dosage form containing one or more excipients with or without active ingredients (e.g., drugs), it is necessary that the material to be compressed into the dosage form possess certain physical characteristics which lend themselves to processing in such a manner. Among other things, the material to be compressed must be free-flowing, must be lubricated, and, importantly, must possess sufficient cohesiveness to insure that the solid dosage form remains intact after compression.

In the case of tablets, the tablet is formed by pressure being applied to the material to be tableted on a tablet press. A tablet press includes a lower punch which fits into a die from the bottom and an upper punch having a corresponding shape and dimension which enters the die cavity from the top after the tableting material fills the die cavity. The tablet is formed by pressure applied on the lower and upper punches. The ability of the material to flow freely into the die is important in order to insure that there is a uniform filling of the die and a continuous movement of the material from the source of the material, e.g. a feeder hopper. The lubricity of the material is crucial in the preparation of the solid dosage forms since the compressed material must be readily ejected from the punch faces.

Since most active agents (e.g., drugs) have none or only some of these properties, methods of tablet formulation have been developed in order to impart these desirable characteristics to the material(s) which is to be compressed into a solid dosage form. Typically, the material to be compressed into a solid dosage form includes one or more excipients, which impart the free-flowing, lubrication, and cohesive properties to the drug(s) and/or other excipient(s) which are being formulated into a dosage form.

Lubricants are typically added to reduce the friction between the compressed tablet and the die wall and to avoid the material(s) being tableted from sticking to the punches. Commonly used lubricants include, e.g., free stearic acid, salts of stearic acid, and sodium stearyl fumarate. Such lubricants are commonly included in the final tableted product in amounts of less than 1% by weight.

In addition to lubricants, solid dosage forms often contain diluents. Diluents are frequently added in order to increase the bulk weight of the material to be tableted in order to make the tablet a practical size for compression. This is often necessary where the dose of the drug is relatively small.

Another commonly used class of excipients in solid dosage forms are binders. Binders are agents which impart cohesive qualities to the powdered material(s). Commonly used binders include, e.g., povidone, hypromellose, copovidone, and hyprolose.

Disintegrants are often included in order to ensure that the ultimately prepared compressed solid dosage form has an acceptable disintegration rate in an environment of use (such as the gastrointestinal tract). Typical disintegrants include cross-linked starch derivatives, salts of cross-linked carboxymethylcellulose and cross-linked povidone.

There are three general methods of preparation of the materials to be included in the solid dosage form prior to compression: (1) dry granulation; (2) direct compression; and (3) wet granulation.

Dry granulation procedures may be utilized where one of the constituents, either the drug or the diluent, has insufficient cohesive or flow properties to be tableted. The method includes mixing the ingredients, slugging the ingredients, dry screening, lubricating and finally compressing the ingredients.

In direct compression, the powdered material(s) to be included in the solid dosage form is compressed directly without modifying the physical nature of the material itself.

The wet granulation procedure includes mixing the powders by mechanical agitation or air-induced fluidization while simultaneously adding solutions of a binding agent to the mixed powders to obtain a granulation. Thereafter, the damp mass is screened, e.g., in a 6- or 8-mesh screen and then dried, e.g., via tray drying, the use of a fluid-bed dryer, radio-frequency dryer, microwave, vacuum, or infra-red dryer.

The use of direct compression is limited to those situations where the drug or active ingredient has a requisite crystalline structure and physical characteristics required for formation of a pharmaceutically acceptable tablet. On the other hand, it is well known in the art to include one or more excipients which make the direct compression method applicable to drugs or active ingredients which do not possess the requisite physical properties. For solid dosage forms wherein the drug itself is to be administered in a relatively high dose (e.g., the drug itself comprises a substantial portion of the total tablet weight), it is necessary that the drug(s) itself have sufficient physical characteristics (e.g., cohesiveness) for the ingredients to be directly compressed.

Typically, however, excipients are added to the formulation in order to impart good flow and compression characteristics to the material as a whole which is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dihydrate, among others.

Due to the popularity of microcrystalline cellulose, pharmaceutical formulators have deemed it desirable to include this excipient in formulations which are wet granulated prior to tableting. Microcrystalline cellulose may also be included in formulations which are directly compressed.

A processed cellulose, microcrystalline cellulose, has been utilized extensively in the pharmaceutical industry as a direct compression vehicle for solid dosage forms. Microcrystalline cellulose is commercially available under the tradenames VIVAPUR® and Emcocel® from JRS Pharma and as Avicel® from Dupont. Compared to other directly compressible excipients, microcrystalline cellulose is generally considered to exhibit superior compressibility and disintegration properties.

Vivapur® MCG is a free flowing powder which is a synergistic, co-processed composite commercially available from JRS Pharma, consisting of microcrystalline cellulose (MCC) and sodium carboxymethylcellulose (Na-CMC). It is a unique suspending and emulsifying agent, which facilitates a wide range of liquid dosage forms. Due to its stabilizing mechanism, Vivapur® MCG can be used with a broad variety of active pharmaceutical ingredients (APIs), offering the opportunity for new applications and line extensions for existing products.

After activation, co-processed microcrystalline cellulose and carboxymethylcellulose sodium ("MCG") builds an opaque-white dispersion, which masks insoluble particles, giving the suspension a homogenous appearance. The dispersed Vivapur® MCG is distinguished by an odorless and tasteless, smooth but not slimy mouth feel, and handles flavors well. Upon agitation, MCG dispersions show a shear rate-dependent decrease in viscosity and become liquid. A complete, time-dependent, regeneration of the viscosity takes place during a subsequent rest period. This thixotropic behavior allows for outstanding sprayability of nasal sprays, effortless dosing through drenches and dispensers, accurate dosage of oral suspensions, hassle-free handling of activated gel, ideal pumpability, smooth and pleasant swallowing without problems, and excellent content uniformity.

Vivapur® MCG is used as a suspending agent, emulsifier, and thickener for oral suspensions, veterinary drenches, nasal sprays, reconstitutable powders, gels, creams, and lotions. Its benefits include easy handling of dry powder, heat stability, compatibility with a wide range of ingredients, stability over a wide pH range, and safe for use for use in animal health products, pediatric suspensions, and nutraceuticals.

U.S Pat. No. 7,879,382 describes compositions that generally include microcrystalline cellulose, salt, and at least one water soluble cellulose ether. The cellulose ether can include those that have a degree of substitution that is about 0.6 to about 1.5. In some embodiments, the cellulose ether comprises an alkali metal (e.g., sodium) carboxymethylcellulose ("CMC"). The microcrystalline cellulose and cellulose ether can be present in a weight ratio from about 50:50 to about 90:10, while the salt is present at a concentration of about 2% to about 6% by dry weight of the composition. The salt may be, e.g., calcium chloride.

Traditionally, solid dosage forms have been manufactured by batch processing, which is sequential step-wise process. In a typical batch processing, various raw materials (active pharmaceutical ingredients (APIs) and excipient are produced at separate facilities and separately shipped to a dosage form facility where they are combined into a dosage form. Batch processing is time consuming as it involves sequential processing and testing of material across multiple discrete stages (and potentially facilities).

OBJECTS AND SUMMARY OF THE INVENTION

It is an object of the present invention to provide a co-processed lubricant which provides a higher bulk density as compared to a traditional lubricant (e.g., not co-processed).

It is another object of the present invention to provide a co-processed lubricant, which possesses an improved flowability as compared to a traditional lubricant (e.g., not co-processed). This feature is one the chief advantages of the present invention, making the co-processed lubricant more suitable, e.g., for continuous manufacturing as compared to a traditional lubricant (e.g., not co-processed). In contrast to batch manufacturing, continuous manufacturing combines the full manufacturing stream into a single, fully integrated flow, may, e.g., eliminate built-in production gaps and has a potential to shorten manufacturing times from months to days.

It is another object of the present invention to provide a co-processed lubricant which can be used to tablet active ingredients, where the excipient can be premanufactured.

It is an additional object of the present invention to provide a co-processed lubricant which when compressed mixed with an active pharmaceutical ingredient (API) and/or other optional ingredients will result in tablets having a higher tablet hardness as compared to tablets which contain a traditional lubricant (e.g., not co-processed) in the (otherwise similar) formulation.

It is an object of the present invention to provide tablets produced with a co-processed lubricant which provides a comparable disintegration time as a tablet which contains a traditional lubricant (e.g., not co-processed) in the (otherwise similar) formulation, even though the tablets are harder.

It is a further object of the present invention to provide a co-processed lubricant which allows for continuous manufacturing, e.g., by direct compression of one or more excipients with or without one or more active ingredients.

It is a further object of the present invention to provide a solid dosage form which includes the improved co-processed excipient of the present invention.

It is a further object of the present invention to provide tablets produced with a co-processed lubricant which provides a comparable disintegration time as a tablet which contains a traditional lubricant (e.g., not co-processed) in the (otherwise similar) formulation, even though the tablets are harder.

It is a further object of the present invention to enable manufacture of and provide an oral solid dosage form which is economical to manufacture, which maintains its integrity during storage, and which possesses excellent disintegration and dissolution properties when exposed, e.g., to gastrointestinal fluid. The tablets may consist of one or more excipients or comprise one or more excipients and one or more active ingredients (e.g., drugs).

In accordance with the above objects and others which will be obvious to those skilled in the art, the present invention is directed to an excipient which comprises or consists of a pharmaceutically acceptable lubricant co-processed with a co-processed combination of microcrystalline cellulose and an alkali metal cellulose ether (e.g., sodium carboxymethylcellulose). The co-processed lubricant is suitable for incorporation into solid dosage forms (e.g., tablets and capsules). In certain embodiments, the excipient further comprises or consists of one or more additional pharmaceutically acceptable excipients used in tablet formulations.

In certain embodiments, the microcrystalline cellulose and alkali salt of a cellulose ether are in intimate association with each other (e.g., are co-processed), in the form of agglomerated particles, e.g., as attainable via a spray-drying technique, prior to being co-processed with the pharmaceutically acceptable lubricant.

In certain embodiments, the microcrystalline cellulose, cellulose ether (e.g., MCG (microcrystalline cellulose/sodium carboxymethylcellulose)) and pharmaceutically acceptable lubricant are co-processed to obtain agglomerated particles comprising or consisting of these ingredients in a single co-processing step, e.g., as attainable via a spray-drying technique.

In certain preferred embodiments, the pharmaceutically acceptable lubricant comprises or consists of stearates of alkaline earth metals (e.g., magnesium stearate), alkali cellulose ethers, sodium stearyl fumarate, or mixtures thereof.

In certain preferred embodiments, the cellulose ether is an alkali metal cellulose ether, most preferably sodium carboxymethylcellulose.

In certain preferred embodiments, where a (previously) co-processed microcrystalline cellulose/alkali metal cellulose ether (e.g., MCG (microcrystalline cellulose/sodium carboxymethylcellulose) is co-processed with a pharmaceutically acceptable lubricant. Prior to co-processing with the lubricant, the previously co-processed microcrystalline cellulose/alkali metal cellulose ether comprises from about 11.3% to about 18.8% alkali metal cellulose ether (e.g., sodium carboxymethylcellulose) and from about 81.2% to about 88.7% microcrystalline cellulose by weight. In such embodiments, the co-processed excipient preferably comprises agglomerated particles. In certain preferred embodiments, the lubricant and MCG weight ratio ranges from about 1:99 to about 99:1, more preferably from about 40:60 to about 90:10, most preferably from about 60:40 to about 80:20. In some of these embodiments, the lubricant and MCG weight ratio is about 70:30. In preferred embodiments, agglomerated particles of co-processed microcrystalline cellulose/alkali metal cellulose ether, and pharmaceutically acceptable lubricant comprise, by weight, from about 0.8 to about 88% microcrystalline cellulose, from about 0.1 to about 19% cellulose ether, and from about 1 to about 99% lubricant, and most preferably from about 8 to about 54% microcrystalline cellulose, from about 1 to about 12% cellulose ether, and from about 40 to about 90% lubricant. The agglomerated particles may have an average particle size, e.g., of from about 10 microns to about 1,000 microns, more preferably from about 10 microns to about 500 microns.

In certain preferred embodiments, the degree of substitution of the preferred cellulose ether (sodium carboxymethylcellulose) is from about 0.7 to about 1.2.

The present invention is also directed in part to an aqueous suspension comprising or consisting of a microcrystalline cellulose, a cellulose ether, and a pharmaceutically acceptable lubricant. In certain preferred embodiments where the microcrystalline and cellulose ether are previously co-processed prior to incorporation of the lubricant, the suspension is prepared by adding the requisite amount of water to the dry mixture of the powders (e.g., MCG and lubricant). For example, in preferred embodiments the dry mixture may comprise about 70% lubricant and about 30% MCG by weight. In certain preferred embodiments, the water content, by weight, is from about 50% to about 99% of the suspension, more preferably from about 80 to about 98% of the suspension and most preferably about 95% of the suspension. The percentage of MCG by weight in the suspension is from about 1% to about 3%, but most preferably about 1.5%, and the percentage of lubricant by weight is from about 1% to 20%, but most preferably about 3.5% (with the lubricant preferably being a stearate of an alkaline earth metal or mixtures thereof). In certain preferred embodiments, the solids content of the aqueous suspension is from about 1% to about 50%, by weight, more preferably from about 2% to about 20% by weight and most preferably about 5%.

In certain embodiments, the excipient composition is a physical admixture comprising microcrystalline cellulose, cellulose ether and lubricant, although it is preferred that these ingredients are co-processed such that the final excipient product comprises agglomerated particles of (at least) these ingredients plus any optional pharmaceutical excipients.

In certain embodiments, the present invention may be co-processed with other excipients such as filler-binders, disintegrants and flow-aid-excipients. In these embodiments, the excipient may be an agglomerated particle comprising a microcrystalline cellulose, a cellulose ether, a lubricant and one or more additional excipients selected from the group consisting of filler-binders, disintegrants and flow-aid-excipients.

In certain preferred embodiments wherein the excipient composition comprises a particulate agglomerate as described in the above paragraphs, the excipient composition is prepared by preparing an aqueous slurry of microcrystalline cellulose in the form of a wet cake with other optional pharmaceutically acceptable ingredients, and spray-drying the microcrystalline cellulose and cellulose ether together to form agglomerated particles comprising the same and thereafter spray-drying the microcrystalline cellulose/cellulose ether co-processed agglomerated particles together with the pharmaceutically acceptable lubricant to obtain the final co-processed excipient product of the present invention.

The invention is further directed in part to a pharmaceutical solid dosage form, comprising an excipient composition comprising a co-processed excipient of microcrystalline cellulose, a pharmaceutically acceptable cellulose ether, and a pharmaceutically acceptable lubricant as described above. In some of these embodiments, the pharmaceutical solid dosage form is a placebo formulation.

The invention is further directed in part to a pharmaceutical solid dosage form, comprising an excipient composition comprising a co-processed excipient of microcrystalline cellulose, a pharmaceutically acceptable cellulose ether, and a pharmaceutically acceptable lubricant as described above; and from 0% to about 99%, or from about 1% to about 95%, and in certain embodiments more preferably from about 10% to about 92% of an active ingredient. The solid dosage form may further comprise optional or additional pharmaceutical excipients such as those described in later paragraphs. In certain preferred embodiments, the solid dosage form is a compressed tablet, i.e., the co-processed excipient composition of the present invention is mixed together with an active ingredient(s), other optional or additional pharmaceutical excipients, and then compressed into tablets. In certain embodiments, the active ingredient(s) is first mixed with one or more pharmaceutical excipients, and then the resulting mixture is mixed with the excipient composition of the present invention. The ingredients may be formulated into compressed tablets by physical admixture of the ingredients followed by compression into tablets, wet or dry granulation followed by compression into tablets, or the active ingredient may be adsorbed onto the surface of the co-processed excipient composition, followed by compression into tablets. The compression into tablets step may be accomplished by any means known to those skilled in the art. In certain embodiment the ingredients are formulated into compressed tablets by direct compression. Alternatively, the mixture of co-processed excipient and active agent may be incorporated in granular or powder form into a capsule. The compressed solid dosage form provides a suitable immediate release dissolution profile of the active ingredient(s) when exposed to aqueous solutions during in-vitro dissolution testing, and provides a release of drug in an environment of use which is considered bioavailable. In further embodiments of the invention, the dissolution profile of the solid dosage form is modified to provide a controlled or sustained release dissolution profile.

The present invention is further directed to a granulate of the novel pharmaceutical excipient described herein and a mixture of an active ingredient(s) and one or more optional or additional pharmaceutical excipient(s), wherein the active ingredient(s) and one or more optional or additional pharmaceutical excipient(s) have been subjected to a wet granulation procedure prior to being granulated with the novel pharmaceutical excipient.

The present invention is further directed to a compressed solid dosage form comprising an active ingredient(s) and the novel pharmaceutical excipient described herein, wherein the active ingredient(s) and excipient have been directly compressed into the solid dosage form.

The present invention is further directed in part to a method of preparing an improved pharmaceutical lubricant, comprising mixing together a pharmaceutically acceptable lubricant together with microcrystalline cellulose and a cellulose ether in an aqueous suspension and spray-drying the mixture to obtain solid agglomerated particles of the microcrystalline cellulose, cellulose ether and pharmaceutically acceptable lubricant. The amount of microcrystalline cellulose/cellulose ether in the suspension by weight is from about 1% to about 3% of the suspension, the amount of pharmaceutically acceptable lubricant is from about 1% to about 20% of the suspension and the water content of the aqueous suspension is from about 80% to about 98%. The microcrystalline cellulose and cellulose ether may be co-processed to provide agglomerated excipient particles prior to incorporation into the aqueous suspension. The resultant solid agglomerated particles may be mixed with an active ingredient and, if necessary, optional and/or additional excipients, and compressed into a tablet. In certain preferred embodiments, the cellulose ether is an alkali metal cellulose ether such as sodium carboxymethylcellulose and the pharmaceutically acceptable lubricant is a stearate of an alkaline earth metal or mixtures thereof.

Definitions

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced item.

The term "about" is used synonymously with the term "approximately." The use of the term "about" with respect to doses and amounts indicates that values slightly outside the cited values, i.e., plus or minus 0.1% to 20%.

An "active agent" is any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. The terms "active agent" and "drug" are used synonymously herein.

The term "co-processed" as it is used herein means that the stated ingredients have been processed together such that the resultant mixture comprises agglomerated particles of the ingredients, which are in intimate association with each other, and the co-processing encompasses any process known to those skilled in the pharmaceutical arts to obtain such agglomerated particles.

By "controlled release" or "sustained release" it is meant for purposes of the invention that the therapeutically active medicament is released from the formulation at a controlled rate such that therapeutically beneficial blood levels (but below toxic levels) of the medicament are maintained over an extended period of time, e.g., providing a 12 hour or a 24 hour dosage form.

By "bioavailable" it is meant for purposes of the invention that the therapeutically active medicament is absorbed from the formulation and becomes available in the body at the intended site of drug action.

"Pharmaceutical compositions" are compositions comprising at least one active agent (drug), such as a compound or salt, solvate, or hydrate of an active agent, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form.

"Pharmaceutically acceptable" refers to those properties and/or substances that are acceptable to a human patient from a pharmacological/toxicological point of view and to the manufacturing pharmaceutical chemist from a physical/chemical point of view regarding composition, formulation; stability, patient acceptance and bioavailability.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As one of ordinary skill in the art will appreciate, the terms "microcrystalline cellulose in the form of a wet cake", "hydrocellulose", and "hydrolyzed cellulose" are synonymous, and refer to the precursor of the (dried) microcrystalline cellulose product.

BRIEF DESCRIPTION OF THE DRAWINGS

The following drawings are illustrative of embodiments of the invention and are not meant to limit the scope of the invention as encompassed by the claims.

Figure 3:
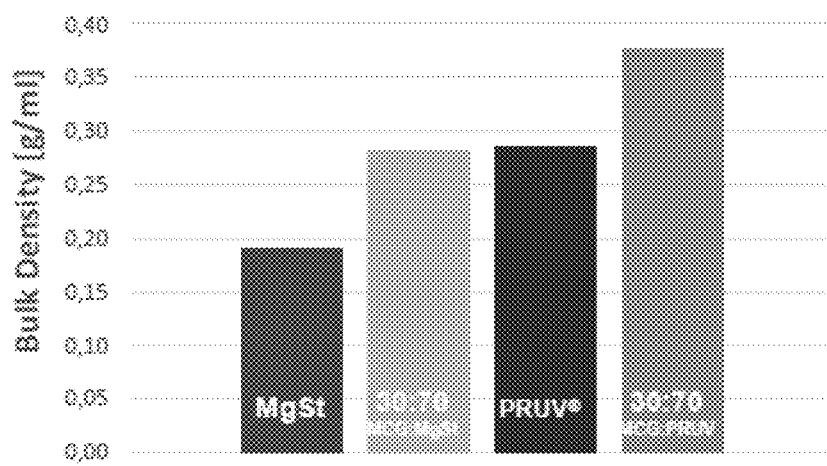
Figure 4:
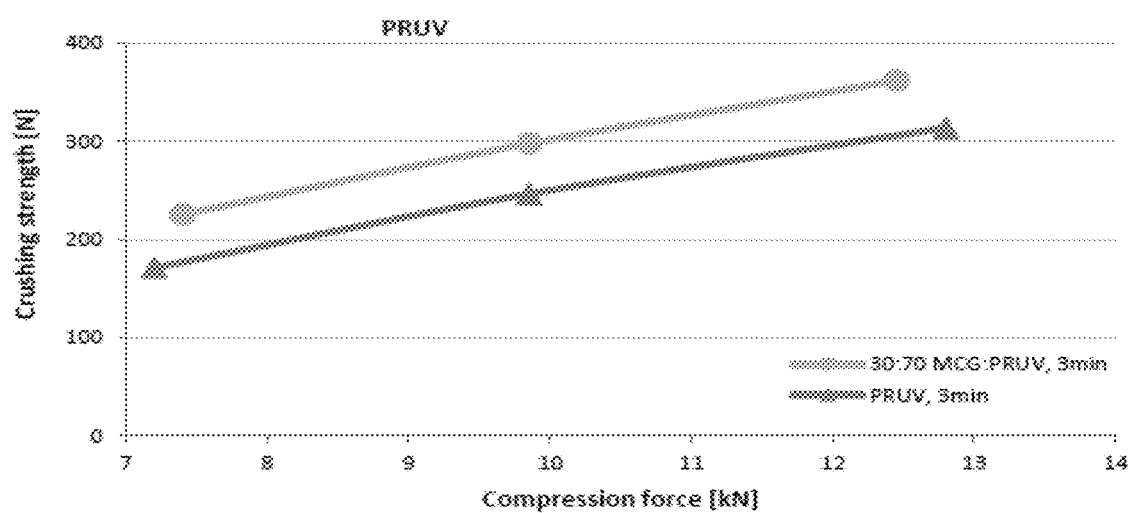

FIG. 3 graphically shows the Bulk Density for Examples 2A and 2B, as compared to plain lubricant (Pruv® and magnesium stearate, respectively);

FIG. 4 graphically shows crushing strength plotted against compression force for tablets containing 30:70 MCG (Vivapur® 102):Pruv® and tablets containing plain Pruv®.

Figure 5:
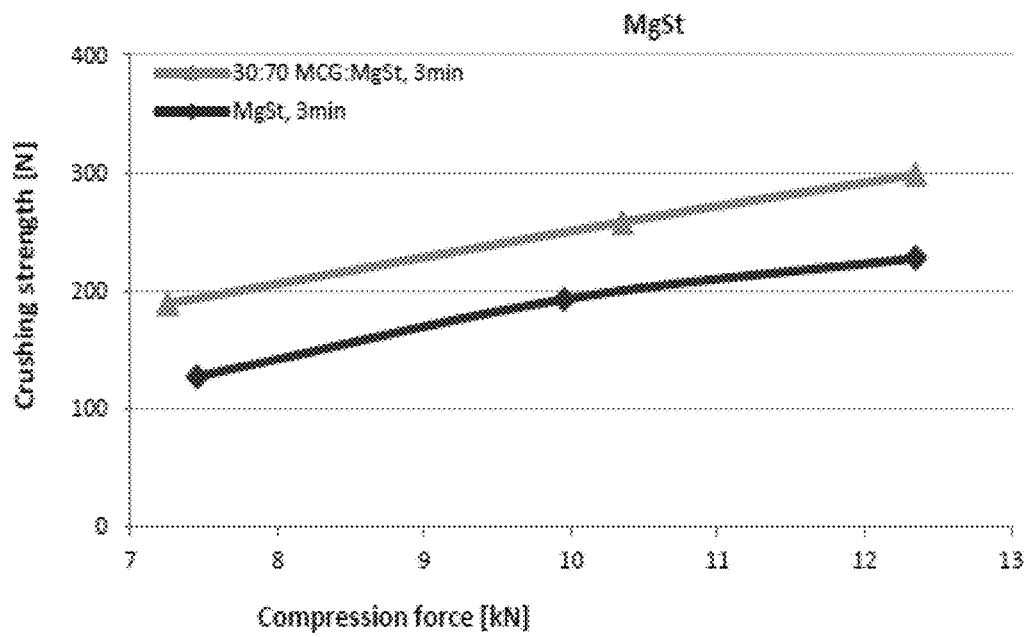
Figure 6:
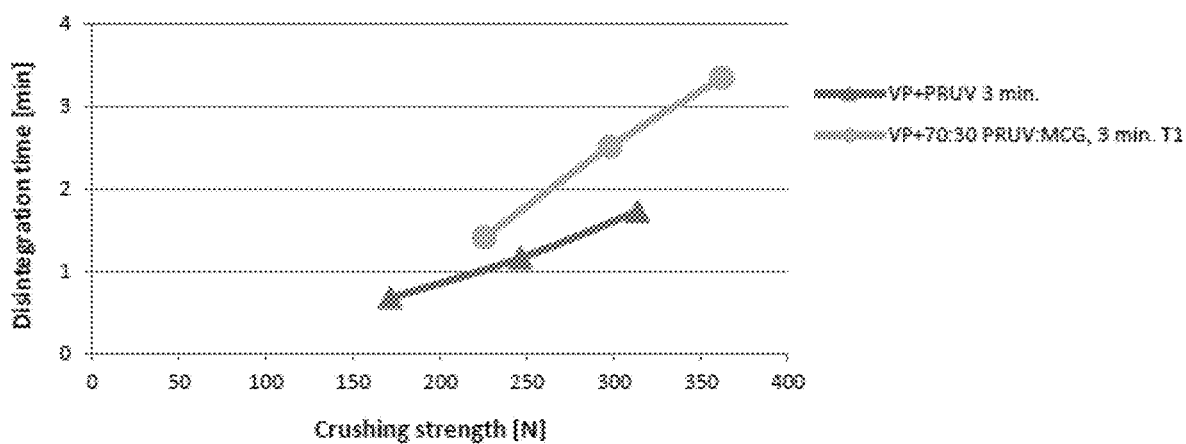
Figure 7:
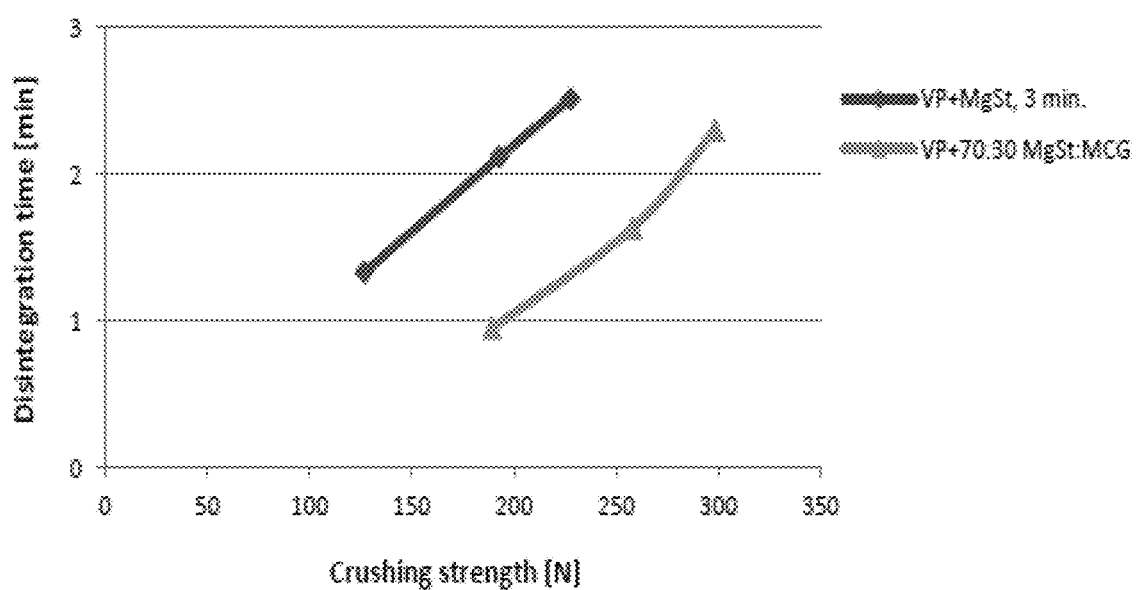

FIG. 5 graphically shows crushing strength plotted against compression force for tablets containing 30:70 MCG (Vivapur® 102):magnesium stearate and tablets containing plain magnesium stearate;

FIG. 6 graphically shows disintegration time [minutes] plotted against the crushing strength [N] for tablets containing 30:70 MCG (Vivapur® 102):Pruv® and tablets containing plain Pruv®; and FIG. 7 graphically shows disintegration time [minutes] plotted against the crushing strength [N] for tablets containing 30:70 MCG (Vivapur® 102):magnesium stearate and tablets containing plain magnesium stearate.

DETAILED DESCRIPTION OF THE INVENTION

The present invention is directed in part to a new co-processed excipient which can be used to provide improved flowability and utilized in continuous manufacturing. As compared to a conventional pharmaceutically acceptable lubricant which has not been co-processed as per the present invention prior to the incorporation into a dosage form, the co-processed excipient has a higher bulk density. In certain embodiments, the bulk density of the co-processed excipient allows for the incorporation and use of the co-processed excipient in continuous manufacturing.

The co-processed excipient may also allow for an increased tablet hardness (harder tablets can be produced with the co-processed excipient of the present invention), and comparable disintegration time of the tablets prepared with the co-processed lubricant as compared with tablets formulated with the same lubricant which has not been co-processed as per the present invention, even though the tablets prepared using the new co-processed excipient (with the co-processed lubricant) are harder. The excipient comprises microcrystalline cellulose, a cellulose ether, and a pharmaceutically acceptable lubricant.

Microcrystalline cellulose is a well-known tablet diluent. Its chief advantage over other excipients is that it can be directly compressed into self-binding tablets which disintegrate rapidly when placed into water. This widely-used ingredient is prepared by partially depolymerizing cellulose obtained as a pulp from fibrous plant material with dilute mineral acid solutions. Following hydrolysis, the hydrocellulose thereby obtained is purified via filtration and the aqueous slurry is spray dried to form dry, white odorless, tasteless crystalline powder of porous particles of a broad size distribution. In this regard, one of ordinary skill in the art will appreciate that the terms "hydrolyzed cellulose", "hydrocellulose", and "microcrystalline cellulose in the form of a wet cake" are synonymous and encompass materials prepared by partially depolymerizing cellulose obtained as pulp. Another method of preparing microcrystalline cellulose is disclosed in U.S. Pat. No. 3,141,875. This reference discloses subjecting cellulose to the hydrolytic action of hydrochloric acid at boiling temperatures so that amorphous cellulosic material can be removed and aggregates of crystalline cellulose are formed. The aggregates are collected by filtration, washed with water and aqueous ammonia and disintegrated into small fragments, often called cellulose crystallites by vigorous mechanical means such as a blender. Microcrystalline cellulose is commercially available in several grades that range in average particle size from 20 to 200 microns.

Any microcrystalline cellulose known to those skilled in the art as being useful in tablet formulations may be used in the co-processed excipient formulations of the present invention. The microcrystalline cellulose used in the present invention may be derived, e.g., from wood pulp, corn husks, bagasse, straw, cotton, cotton linters, flax, kemp, ramie, fermented cellulose, etc. Preferably, the microcrystalline cellulose is pharmaceutically acceptable, i.e., approved for consumption by a regulatory agency such as the U.S. Food and Drug Administration.

Microcrystalline cellulose is water-insoluble, but the material has the ability to draw fluid into a tablet by capillary action. The tablets then swell on contact and the microcrystalline cellulose thus acts as a disintegrating agent. The material has sufficient self-lubricating qualities so as to allow a lower level of lubricant as compared to other excipients. Typically, microcrystalline cellulose has an apparent density of about 0.28 $g/cm^3$ and a tap density of about 0.43 $g/cm^3$.

When utilized in pharmaceutical applications, microcrystalline cellulose is typically used as a tablet binder/diluent in wet granulation and direct compression formulations in amounts of about 5-30% of the formulation, or more. However, it is known to use more or less microcrystalline cellulose in pharmaceutical products, depending upon the requirements of the formulation.

Cellulose ethers which can be used in the co-processed excipients of the present invention include but are not limited to water soluble cellulose ethers, and most preferably are an alkali metal carboxymethylcellulose such as sodium or potassium carboxymethylcellulose ("CMC"), and most preferably sodium carboxymethylcellulose. In other embodiments of the invention, the cellulose ether may be methylcellulose, methylhydroxyethylcellulose, methylhydoxypropylcellulose, hydroxyethylcellulose, and ethoxyhydroxyethylcellulose. The cellulose ether can be a single cellulose ether (e.g., sodium carboxymethylcellulse), or combinations of any of foregoing. Where the cellulose ether is sodium CMC, the degree of substitution of the pharmaceutical grades of CMC range from about 0.7 to about 1.2.

In certain embodiments, the microcrystalline cellulose in the co-processed excipient is a functionalized product such a silicified microcrystalline cellulose such as, e.g., Prosolv®.

When the microcrystalline cellulose and cellulose ether are incorporated as a premanufactured, co-processed excipient such as Vivapur® MCG, the percentages of CMC present on MCG are fixed by its specification. They range from about 11.3% to about 18.8% CMC.

The primary function of lubricants in tableting is to reduce the force required to eject the compressed tablet from the die cavity. Also, lubricants strongly influence tablet hardness, disintegration time, and dissolution. Preferably, the lubricant is a pharmaceutically acceptable lubricant. Lubricants for use in the formulations of the present invention include lubricants commonly used in the formulation of pharmaceuticals. Examples of lubricants for use in accordance with the present invention include but are not limited to magnesium carbonate, magnesium lauryl sulfate, calcium silicate, talc, fumed silicon dioxide, magnesium stearate, calcium stearate, stearic acid, sodium stearyl fumarate, polyethylene glycols, sodium lauryl sulfate, magnesium lauryl sulfate, sodium benzoate, colloidal silicon dioxide, magnesium oxide, microcrystalline cellulose, starches, mineral oil, waxes, glyceryl behenate, polyethylene glycol, palmitic acid, calcium stearate, carnauba wax, hydrogenated vegetable oils, sodium acetate, sodium chloride, combinations thereof, and the like. Examples of preferred pharmaceutically acceptable lubricants are magnesium stearate and sodium stearyl fumurate (commercially available as Pruv® from Applicant JRS Pharma). Other suitable lubricants and additional excipients which may be used are described in Handbook of Pharmaceutical Excipients, $2^{nd}$ Edition, American Pharmaceutical Association; The Theory and Practice of Industrial Pharmacy, $2^{nd}$ Edition, Lachman, Leon, 1976; Pharmaceutical Dosage Forms: Tablets Volume 1, $2^{nd}$ Edition, Lieberman, Hebert A., et al, 1989; Modern Pharmaceutics, Banker, Gilbert and Rhodes, Christopher T, 1979; and Remington's Pharmaceutical Sciences, 15th Edition, 1975.

The amount of lubricant in the co-processed excipient may range from about 50% to about 95% (w/w), more preferably from about 60% to about 80% (w/w) and most preferably is about 70% of the co-processed excipient formulation.

In addition to the above ingredients, the co-processed pharmaceutical excipient of the present invention may include additional (pharmaceutically acceptable) excipient ingredients that do not materially affect its properties.

The novel co-processed (agglomerated) excipient optionally utilizes a compressibility augmenting agent which (i) physically restricts the proximity of the interface between adjacent cellulose surfaces; (ii) inhibits interactions between adjacent cellulose surfaces, for example, via the creation of a hydrophobic boundary at cellulose surfaces; or (iii) accomplishes both (i) and (ii) above. Compressibility augmenting agents which create physical barriers between microcrystalline cellulose surfaces include silicon dioxide having a very fine particle size, e.g., from about 1 nm to about 100 microns. A most preferred silicon dioxide is colloidal silicon dioxide. Alternatively or additionally, the compressibility augmenting agent may be a surfactant having an HLB value of at least 10, and preferably at least about 15. In certain preferred embodiments, the HLB value of the surfactant is from about 15 to 50 and the surfactant may be an alkyl sulfate such as sodium lauryl sulfate. Highly polar molecules having the requisite HLB value range set forth above may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail) which "points away" from the cellulose surface and discourages hydrophilic surface-to-surface cellulose interactions, such as hydrogen-bonding. Preferably, the dye is one which is pharmaceutically acceptable for inclusion in solid dosage forms. Other compressibility augmenting agents encompassed herein include calcium carbonate. In certain embodiments, microcrystalline cellulose or a functionalized microcrystalline cellulose (e.g., Prosolv® MCG).

Process of Preparation of the Co-Processed Excipient Formulation

In certain preferred embodiments, the microcrystalline cellulose and the cellulose ether are co-processed together prior to the incorporation of the lubricant (e.g., by further co-processing). One skilled in the art will appreciate that this can be accomplished by using a previously manufactured, off-the-shelf excipient product such as Vivapur® MCG, commercially available from Applicant JRS Pharma.

In the present invention, the MCC and cellulose ether are co-processed with the lubricant. As previously stated above, the MCC and cellulose ether can be pre-co-processed prior to the incorporation of the lubricant, or these three components may be co-processed in a single step. The prepared suspension for the spray-drying may contain 1.5% of MCG and 3.5% lubricant. The rest of the suspension (95%) may comprise or consist of water.

The process for preparing the co-processed pharmaceutical excipient composition involves forming a well-dispersed aqueous slurry of microcrystalline cellulose, the cellulose ether, and optionally the lubricant. The slurry may be formed by using microcrystalline cellulose wetcake formed in the hydrolysis step during the manufacture of microcrystalline cellulose, or in may be formed by re-slurrying dried microcrystalline cellulose. The relative amounts of the two components are adjusted in the slurry to yield the specific weight ratio desired in the final dried co-processed composition. The aqueous slurry may be prepared by first preparing the slurry of microcrystalline cellulose and thereafter adding the cellulose ether and/or the lubricant, or by mixing these ingredients together in a (e.g., pharmaceutically acceptable) aqueous medium to form the aqueous slurry.

After a uniform mixture of the ingredients is obtained in the slurry (suspension), the suspension is dried to provide a plurality of microcrystalline cellulose-based excipient particles having enhanced compressibility. Preferably, the slurry is dried using spray-drying techniques, which are well known to those skilled in the art. Other drying techniques, however, such as flash drying, ring drying, tray drying, vacuum drying, radio frequency drying, and microwave drying, may be alternatively used.

The microcrystalline cellulose is preferably wetcake from a conventional microcrystalline cellulose manufacturing process. Wetcake is microcrystalline cellulose that has not yet been dried to yield conventional microcrystalline cellulose as a free-flowing powder. The particle size of the microcrystalline cellulose used in the aqueous slurry is ordinarily that which is encountered in conventional microcrystalline cellulose manufacture. pH adjustment of the wetcake can be made before, during, or after the sugar alcohol addition, preferably before, as representative of conventional MCC manufacturing processes.

The total solids content of the aqueous slurry is preferably at least 10 wt %, based on the total slurry weight, and is more preferably at least 20 wt % solids. The higher solids content levels are desirable since the amount of water that must be removed during the drying step is accordingly reduced. The upper limit on solids content in the aqueous slurry is typically determined by the operating constraints of the drying apparatus used. With the preferred spray drying procedure, solids contents of about 20-30 wt % are representative for aqueous slurries that can be readily processed. Ambient or elevated slurry temperatures, of from about 10° C. to about 80° C. may be used, and higher slurry temperatures may be desirable with certain types of drying equipment.

The drying of the well-dispersed aqueous slurry is preferably accomplished by spray drying. Conventional spray drying equipment may be used. Operating procedures familiar to those skilled in the spray drying art are applicable to the spray drying step of this process. Drier outlet temperature is ordinarily used to control the residual moisture level obtained in the co-processed composition.

In the spray-drying process, the aqueous dispersion of microcrystalline cellulose (e.g., in the form of a wet cake), cellulose ether and (optionally) the lubricant are brought together with a sufficient volume of hot air to produce evaporation and drying of the liquid droplets. The highly dispersed slurry is pumpable and capable of being atomized. It is sprayed into a current of warm filtered air, which supplies the heat for evaporation and conveys a dried product to a collecting device. The air is then exhausted with the removed moisture. The resultant spray-dried powder particles are approximately spherical in shape and are relatively uniform in size, thereby possessing excellent flowability. The co-processed product comprises or consists of microcrystalline cellulose/cellulose ether as MCG, or further comprises the lubricant (which can be incorporated in one step where the MCG is not premanufactured, or in a separate co-processing step. The final product of excipient particles comprise or consist of microcrystalline cellulose, cellulose ether and lubricant in intimate association with each other, e.g., the particles comprise or consist of an agglomerate of these three ingredients.

Depending upon the amount and type of drying, the co-processed excipient product may have different particle sizes, densities, pH and moisture content. Spray drying is an especially preferred method for removing water from the aqueous slurry and thereby accomplishing the drying step.

Spray drying the well-dispersed aqueous slurry produces a co-processed composition having a loose bulk density of less than or equal to 0.60 g/cm$^3$, suitably 0.15 g/cm$^3$ to 0.60 g/cm$^3$. The loose bulk density may be less than 0.55 g/cm$^3$, less than 0.50 g/cm$^3$, less than 0.45 g/cm$^3$, less than 0.40 g/cm$^3$, less than 0.35 g/cm$^3$, less than 0.30 g/cm$^3$, less than 0.25 g/cm$^3$ and less than 0.20 g/cm$^3$.

The co-processed composition recovered from the drying operation is a free-flowing particulate solid. Particle size of the product is a function of the spray drier settings, which can be controlled by those skilled in the art such as adjusting feed rates and atomizer disc speeds during spray drying.

It is most preferred in the present invention that the microcrystalline cellulose, cellulose ether and lubricant co-processed in either one or two steps as explained above, resulting in an intimate association of these ingredients, rather than being combined, e.g., as a dry mixture.

In certain embodiments of the present invention, the aqueous slurry of the microcrystalline cellulose, cellulose ether, and lubricant are introduced into the spray dryer as a single aqueous medium. However, it is possible to separately introduce each ingredient into separate aqueous medium which are then combined. Other procedures for combining the microcrystalline cellulose in the form of a wet cake (i.e. hydrocellulose or hydrolyzed cellulose) and cellulose ether known to those skilled in the art are deemed to be equivalent to the spray-drying technique described above, and are further deemed to be encompassed by the appended claims.

The average particle size of the excipient of the present invention ranges from about 10 microns to about 1000 microns. Particle sizes of about 10-500 microns are preferred, particle sizes of about 30-250 microns are more preferred and particle sizes of about 40-200 microns are most preferred. It will be appreciated by those of ordinary skill in the art that the drying of the microcrystalline cellulose in the form of a wet cake-silicon dioxide suspension results in a random size distribution of the novel excipient particles being produced. For example, if spray drying techniques are used, droplet size, temperatures, agitation, dispersion, air flow, atomizer wheel speed, etc. will effect final particle size. Furthermore, it is within the scope of the invention to sort or mechanically alter the dried particles according to ranges of particle sizes depending upon end uses. The particle size of the integrated excipient is not narrowly critical, the important parameter being that the average size of the particle must permit the formation of a directly compressible excipient which forms pharmaceutically acceptable tablets.

The excipient of the present invention preferably has a bulk (loose) density ranging from about 0.2 g/ml to about 0.6 g/ml, and most preferably from about 0.35 g/ml to about 0.55 g/ml. The novel excipient preferably has a tapped density ranging from about 0.2 g/ml to about 0.6 g/ml, and most preferably from about 0.35 g/ml to about 0.55 g/ml. The pH of the particles is most preferably about neutral, although granulates having a pH of from about 3.0 to about 8.5 are possible. The moisture content of the excipient particles will preferably broadly range from about 0.5% to about 15%, preferably from about 2.5% to about 6%, and most preferably from about 3.0% to about 5% by weight.

The novel excipient preferably comprises a particulate agglomerate of co-processed microcrystalline cellulose, from about 5% to about 50%, or from about 10% to about 50% and in certain embodiments from about 20% to about 35%, and in other embodiments from about 25% to about 35%, and in certain embodiments preferably from about 12% to about 23% silicate-based adsorbent carrier (e.g., magnesium aluminometasilicate or granular hydrophilic silica), by weight. The novel excipient may optionally further comprise from about 0.1% to about 20%, and preferably from about 0.25% to about 5% compressibility augmenting agent.

The novel excipient in accordance with the invention is free-flowing and directly compressible. Accordingly, the excipient may be mixed in the desired proportion with an active agent and optional lubricant (blended or dry granulated), and then directly compressed into solid dosage forms.

In preferred embodiments, the pharmaceutical co-processed excipient is combined with one or more other excipient(s) with or without an active ingredient(s). Active ingredients which may be incorporated together with the excipient of the present invention include but are not limited to systemically active therapeutic agents, locally active therapeutic agents, nutraceuticals, disinfecting agents, chemical impregnants, cleansing agents, deodorants, fragrances, dyes, animal repellents, insect repellents, a fertilizing agents, pesticides, herbicides, fungicides, and plant growth stimulants, and the like. In certain preferred embodiments, the active agent is one or more drug(s), a food supplement(s), a medical food(s), or a nutraceutical(s). The active agent may be water soluble or water insoluble.

Classes of drugs which may be incorporated with the excipient of the present invention include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, antineoplastic agents, and cholesterol ester transfer protein inhibitors.

The present invention is suitable for preparation of placebo tablets. Placebo tablets do not contain an active ingredient and may, e.g., be used in various clinical trials (e.g., double-blinded clinical trials). In the preferred embodiments, placebo tablets are visually indistinguishable from the tablets comprising an active ingredient and used in the same clinical trial.

The present invention is useful with any drug capable of being formulated as an amorphous drug. The term "drug" is conventional, denoting a compound having beneficial prophylactic and/or therapeutic properties when administered to an animal, especially humans.

The active ingredient(s) may further be any agent that is traditionally used as a medicament and lends itself to being administered through the oral cavity. Such active agents may be, for example, vitamins, chemotherapeutics; antimycotics; oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, psychotherapeutic agents, anti-diabetic agents and cardiovascular agents, nutraceuticals and nutritional supplements. This list is exemplary only, and is not meant to be limiting in any way.

Vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K and Coenzyme Q10.

Example of botanical bioactive agents, are: polyphenols, isoflavones, resveratrol, soy isoflavones, grape seed extract polyphenols, curcumin, epigenin. Anti-inflammatory plant extracts such as aloe vera, echinacea and chamomile hammamelis extracts, anti-psoriatic such as chinese zizipus jujuba. Astringents such as hammamelis anti-bacterial such as artemisia, chamomile, golden seal. Immune modulators such as echinacea, anti-aging or anti-cancer or anti-photo damage, anti-inflammatory such as feverfew parthenolides, rejuvenation agents, carotenoids, beta-carotene, lycopene, astaxanthons, lutein, tocopheryl and retinol.

Coronary drugs include but are not limited to vasodilators such as nitroglycerin, isosorbide dinitrate, Calcium-antagonists such as verapamil, nifedipine and diltiazem, Cardiac-glycosides such as digoxin.

Analgesics include but are not limited to opioid analgesics such as morphine, buprenorphine, oxycodone, oxymorphone, hydromorphone, meperidine, fentanyl, sufentranil, alfentanil, aspirin, acetaminophen, etc; NSAIDs such as naproxen, ibuprofen, diclofenac; Local anesthetics such as lidocaine, bupivacaine, etc.; ergot and ergot derivatives (wigraine, cafergot, ergostat, ergomar, dihydroergotamine), imitrex.

Example of cholesterol and triglycerides lowering drug: fenofibrate, lovastatin, simvastatin, pravastatin, fluvastatin, atorvastatin, or cerivastatin.

Anxiolytics, sedatives and hypnotics include but are not limited to diazepam, nitrazepam, flurazepam, estazolam, flunitrazepam, triazolam, alprazolam, midazolam, temazepam, lormetazepam, brotizolam, clobazam, clonazepam, lorazepam, oxazepam, buspirone, etc;

Migraine relieving agents include but are not limited to sumatriptan, ergotamines and derivatives etc;

Drugs against motion sickness include but are not limited to cinnarizine, anti-histamines, etc;

Anti-emetics include but are not limited to ondansetron, tropisetron, granisetrone, metoclopramide, etc. Others: such as disulfuram, vitamin K, etc.

Examples of chemotherapeutics agents include but are not limited to cisplatin (CDDP), procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Antibiotics drugs include but are not limited to tetracyclines such as tetracycline, doxycycline, oxytetracycline, chloramphenicol etc.; macrolides such as erythromycin and derivatives, etc.;

Antivirals include but are not limited to acyclovir, idoxuridine, tromantadine etc.;

Antimycotics include but are not limited to miconazole, ketoconazole, fluconazole, itraconazole, econazole, terconazole, griseofulvin, and polyenes such as amphotericin B or nystatine etc.;

Anti-amoebics include but are not limited to metronidazole, metronidazole benzoate and tinidazole etc.;

Anti-inflammatory drugs include but are not limited to steroids or NSAID's such as indomethacin, ibuprofen, piroxicam, diclofenac etc.; Anti-allergics: Disodium cromoglycate etc.; Immunosuppressive agents: cyclosporins etc.;

Antimicrobial agents that may be used include but are not limited to naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, β-lactamase inhibitors; meziocillin, piperacillin, aztreonam, norfloxacin, trimethoprim, ceftazidime, ceftriaxone and dapsone.

Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxorudine, foscarnet, ganciclovir, zidovudine, dideoxycytosine, dideoxyinosine, stavudine, famciclovir, didanosine, zalcitabine, rifimantadine, and cytokines.

Antihistamines are represented by but are not limited to cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine.

Decongestants and antitussives include but are not limited to agents such as dextromethorphan, levopropoxyphene napsylate, noscapine, carbetapentane, caramiphen, chlophedianol, pseudoephedrine hydrochloride, diphenhydramine, glaucine, pholcodine, and benzonatate.

Anesthetics include but are not limited to etomidate, ketamine, propofol, and benodiazapines (e.g., chlordiazepoxide, diazepam, clorezepate, halazepam, flurazepam, quazepam, estazolam, triazolam, alprozolm, midazolam, temazepam, oxazepam, lorazepam), benzocaine, dyclonine, bupivacaine, etidocaine, lidocaine, mepivacaine, promoxine, prilocalne, procaine, proparcaine, ropivacaine, tetracaine. Other useful agents may include amobartital, aprobarbital, butabarbital, butalbital mephobarbital, methohexital, pentobarbital, phenobarbital, secobarbital, thiopental, paral, chloral hydrate, ethchlorvynol, clutethimide, methprylon, ethinamate, and meprobamate.

Diuretics include but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprionolactone, canrenone, and potassium canrenoate.

Anti-inflammatories include but are not limited to salicylic acid derivatives (e.g. aspirin) paraminophenol derivative (e.g. acetaminophen) indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone).

Psychotherapeutic agents include but are not limited to thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, eldepryl.

Cardiovascular agents include but are not limited to nitroglycerin, isosorbide dinitrate, sodium nitroprisside, captopril, enalapril, enalaprilat, quinapril, lisinopril, ramipril, losartan, aminone, lirinone, vesnerinone, hydralazine, nicorandil, prozasin, doxazosin, bunazosin, tamulosin, yohimbine, propanolol, metoprolol, nadolol, atenolol, timolol, esmolol, pindolol, acebutolol, labetalol, phentolamine, carvedilol, bucindolol, verapamil, nifedipine, amlodipine and dobutamine.

Anti-neoplastic agents and Immunosuppressants include but are not limited to aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

The therapeutic agent(s) which are incorporated into the formulations of the present invention can be used, for example, in the amounts indicated in the Physician's Desk Reference, or as otherwise known and used by one of ordinary skill in the art.

The co-processed excipient formulations of the present invention may be incorporated into pharmaceutical dosage forms (e.g., tablets) in accordance with the embodiments depicted herein are manufactured by standard techniques. For example, the dosage form may be manufactured by the wet granulation technique. In the wet granulation technique, the drug and carrier are blended using an aqueous or organic solvent, such as denatured anhydrous ethanol, as the granulation fluid. The remaining ingredients can be dissolved in a portion of the granulation fluid, such as the solvent described above, and this latter prepared wet blend is slowly added to the drug blend with continual mixing in the blender. The granulating fluid is added until a wet blend is produced, which wet mass blend is then forced through a predetermined screen and dried in a fluid bed dryer. The dried granules are then sized. Next, the co-processed excipient of the present invention, magnesium stearate, or another suitable lubricant and other excipient materials are added to the drug granulation, and the granulation is put into milling jar sand mixed on a jar mill for 10 minutes. The composition is pressed into a layer, for example, in a Manesty® press or a Korsch LCT press. The intermediate compression typically takes place under a force of about 50-100 Newtons. Final stage compression typically takes place at a force of 3500 Newtons or greater, often 3500-5000 Newtons. The compressed cores are fed to a dry coater press, e.g., Kilian® Dry Coaterpress, and subsequently coated with the wall materials as described herein.

In addition to one or more active ingredients, additional pharmaceutically acceptable excipients (in the case of pharmaceuticals) or other additives known to those skilled in the art (for non-pharmaceutical applications) can be added to the novel excipient prior to preparation of the final product. For example, in addition to the above ingredients, the solid formulations prepared using the novel excipient may also include suitable quantities of pharmaceutical adjuvants, e.g., diluents, plasticizers, lubricants, binders, granulating aids, disintegrants (e.g., sodium starch glycolate (commercially available from JRS Pharma under the tradename Explotab®), colorants, flavorants and glidants that are conventional in the pharmaceutical art. A non-limiting list of suitable adjuvants include spray dried lactose, polyvinylpyrrolidone (PVP), alginates (e.g., commercially available from JRS Pharma under the tradename VIVAPHARM®), talc, magnesium stearate (e.g., commercially available from JRS pharma as Lubri-Prez™), and mixtures thereof. The quantities of these additional materials will be sufficient to provide the desired effect to the desired formulation. Other examples of pharmaceutically acceptable carriers and excipients that may be used to formulate oral dosage forms are described in the Handbook of Pharmaceutical Excipients, American Pharmaceutical Association (1986), incorporated by reference in its entirety.

A non-limiting list of plasticizers includes include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used.

For example, if necessary, any generally accepted soluble or insoluble inert pharmaceutical filler (diluent) material can be included in the final product (e.g., a solid dosage form). Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, "off-the-shelf" microcrystalline cellulose, mixtures thereof, and the like. An effective amount of any generally accepted pharmaceutical lubricant, including the calcium or magnesium soaps may optionally be added to the novel excipient at the time the medicament is added, or in any event prior to compression into a solid dosage form. The lubricant may comprise, for example, magnesium stearate in any amount of about 0.5-3% by weight of the solid dosage form.

The complete mixture, in an amount sufficient to make a uniform batch of tablets, may then subjected to tabletting in a conventional production scale tabletting machine at normal compression pressures for that machine, e.g., about 1500-10,000 lbs/sq in. The mixture should not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally. It is contemplated that for certain uses, e.g., antacid tablets, vaginal tablets and possibly implants, that the tablet will be larger.

In certain embodiments, the tablets comprise a compression coated tablet, in which the active substance is contained within a core which is contained within an outer coating (either hydrophobic coating or hydrophilic coating, e.g., as described below). In some embodiments, the coating may be complete, in other embodiments, the coating may be partial.

In certain embodiments of the present invention, the novel excipient and oily active ingredient are further prepared with one or more controlled or sustained release carriers to provide a delayed or sustained release of the active ingredient from the final product (e.g., oral tablet). This can be accomplished, e.g., by incorporating a sustained release carrier(s) together with the mixture of the novel excipient and oily drug(s) (with further optional active ingredients and or further optional pharmaceutically acceptable excipients) and then tableting the mixture, thereby obtained sustained release matrix tablets. On the other hand, the novel excipient and oily drug(s) (with further optional active ingredients and or further optional pharmaceutically acceptable excipients) may be tableted or filled into a capsule, which is then coated with one or more delayed (e.g., enteric) or sustained release carriers to thereby provide a delayed or sustained release final formulation.

In certain embodiments of the invention, the tablet is coated with a sufficient amount of a hydrophobic polymer to render the formulation capable of providing a release of the active ingredient(s) such that a 12 or 24 hour formulation is obtained. The hydrophobic polymer which included in the tablet coating may be the same or different material as compared to the hydrophobic polymeric material which is optionally granulated with the sustained release excipient.

In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit®L 100-555.

In further embodiments, the dosage form may be coated with a hydrophilic coating in addition to or instead of the above-mentioned coatings. An example of a suitable material which may be used for such a hydrophilic coating is hydroxypropylmethylcellulose (e.g., Opadry®, commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60-70° C. for about 3-4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

The coatings which may be optionally applied to the compressed solid dosage form of the invention may comprise from about 0.5% to about 30% by weight of the final solid dosage form.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10 microns if applied via spray-coating or immersion-coating. Generally, in embodiments of the invention wherein a hydrophobic polymer or enteric coating is applied to the tablets, the tablets are coated to a weight gain from about 1% to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In other embodiments of the invention which provide a sustained release product, the sustained-release carrier may be incorporated in a sustained-release matrix to impart sustained-release of the active agent from the final formulation. The sustained release carrier may be hydrophobic or hydrophilic. Suitable materials which may be included in the sustained release carrier of the present invention include alkylcelluloses such as natural or synthetic celluloses derivatives (e.g. ethylcellulose), acrylic and methacrylic acid polymers and copolymers, zein, and mixtures thereof. Suitable biocompatible, preferably biodegradable polymers can be utilized as the sustained release carrier. The biodegradable polymeric material may comprise a polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like.

In yet other preferred embodiments, sustained-release carrier comprises a synthetic or naturally occurring gum. Examples of naturally occurring gums include, e.g., the heteropolysaccharides and homopolysaccharides. An especially preferred heteropolysaccharide is xanthan gum, which is a high molecular weight (>10$^6$) heteropolysaccharide. Other preferred heteropolysaccharides include derivatives of xanthan gum, such as deacylated xanthan gum, the carboxymethyl ether, and the propylene glycol ester. The homopolysaccharides useful in the present invention include galactomannan gums, which are polysaccharides composed solely of mannose and galactose. Preferred galactomannan gums are those which are capable of cross-linking with the heteropolysaccharide. In particular, galactomannans which have higher proportions of unsubstituted mannose regions have been found to achieve more interaction with the heteropolysaccharide when exposed to an environmental fluid. Locust bean gum, which has a higher ratio of mannose to galactose, is especially preferred as compared to other galactomannans such as guar and hydroxypropyl guar. Other natural or synthetic gums known to those skilled in the food and pharmaceutical arts are also useful as the controlled release carrier of the invention. Such gums include alginic acid derivatives, carageenan, tragacanth, acacia, karaya, guar gum, agar, acacia, galactans, mannans, and the like. Water swellable polymers may be used in addition to or instead of gums to promote sustained-release of the active agent from the final formulation. Such water swellable polymers include cellulose ethers, carboxyvinyl polymer and the like.

Optionally, the sustained-release carrier includes a release modifying agent. A release modifying agent according to the invention includes any pharmaceutically acceptable substance which may alter, e.g. prolong or increase, the release rate of the active agent form the formulation upon exposure to an aqueous environment, e.g. gastric fluid or dissolution medium. Suitable release modifying agents which may be incorporated into the matrix formulations of the present invention include, e.g., monovalent or multivalent metal cations. Preferably, the salts are inorganic salts, including e.g., alkali metal and/or alkaline earth metal sulfates, chlorides, borates, bromides, citrates, acetates, lactates, etc. In particular, these salts include, e.g., calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. In preferred embodiments, the release modifying agents are bivalent. Particularly preferred salts are calcium sulfate and sodium chloride. Other release modifying agents include sugars, e.g. sucrose, starches, water-soluble alkylcellulose derivatives such as hydroxypropylmethylcellulose, urea, and the like.

In those embodiments including a release modifying agent any effective amount may be employed (generally from about 0.1% to about 20%, by weight).

The final sustained-release oral dosage form may contain from about 1 to about 99% (by weight) of sustained release carrier. Preferably, the weight percent of the sustained release carrier ranges from about 1 to about 80%.

In certain preferred embodiments of the present invention, the sustained release carrier is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the sustained-release carrier may further include a relatively hydrophilic material, including but not limited to materials such as hydroxyalkylcelluloses such as hydroxypropylmethylcellulose and mixtures of the foregoing.

In yet another embodiment of the present invention, the sustained release carrier(s) (with or without optional release modifying agent(s)) is added into the aqueous slurry of the novel excipient, and the aqueous slurry is then dried in such a manner as to obtain agglomerated sustained release particles.

In certain embodiments of the present invention, the tablet core includes an additional dose of the same or different active ingredient in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857-884, hereby incorporated by reference), stabilizers, binders, odor controlling agents, and preservatives.

The excipient of the present invention provides significant advantages over the prior art with respect to oily active agents or drugs dissolved in an oil. For example, the excipient allows for a manufacturer to switch from expensive and slow soft-gel production to tableting. Also, physical stability issues often found with soft-gel capsules are avoided. Further, oily active agents can be administered in solution in a more dispersed fashion from a tablet than may be formulated to disintegrate faster than a bolus oil dose may disperse. Alternatively, the novel excipient can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

Detailed Description Of The Preferred Embodiments

The following examples illustrate various aspects of the present invention. They are not to be construed to limit the claims in any manner whatsoever.

EXAMPLE 1

A one kilogram batch of the co-processed excipient formulation of the present invention may be prepared as follows: First, a suspension consisting of 300 g of Vivapur® MCG (co-processed microcrystalline cellulose/sodium carboxymethylcellulose)(300 g MCG correspond to 1.5% of the suspension to be prepared) and 700 g Lubricant (magnesium stearate (MgSt) or sodium stearyl fumarate (PRUV®)(700 g lubricant correspond to 3.5% of the suspension) is prepared by adding a sufficient amount of water to the dry mixture of the powders of MCG and lubricant. 19 kg water (95% of the suspension) is added to the dry mixture of the powders MCG and lubricant. All water content will evaporate during the spray-drying process, so the final product will have the desired proportion of 30:70 (MCG: lubricant).

Both powders (MCG and lubricant) preferably are mixed first, and then water is added to form the suspension.

The suspension is subsequently sprayed into the spray-drying tower and water will evaporate completely. The final product comprises co-processed (agglomerated) particles of the co-processed excipient product, the agglomerated particles consisting of MCG and lubricant in the desired 30:70 ratio.

EXAMPLE 2—POWDER PROPERTIES

In Example 2, the properties of the present invention, a co-processed excipient (30:70 MCG:lubricant), are compared to those of the non-co-processed lubricant ("plain lubricant"). To carry out those tests the powder of Magnesium Stearate or PRUV or their co-processed analogues were used. No formulation or any other excipients were added to characterize the powder properties.

In Example 2A, a co-processed excipient containing Pruv® as the lubricant is prepared in similar fashion as set forth in Example 1. In Example 2B, a co-processed excipient containing magnesium stearate as the lubricant is prepared in similar fashion as set forth in Example 1.

The co-processed excipients of Examples 2A and 2B are then examined with respect to the Angle of Repose, Flodex, and Bulk Density. For angle of repose measurement, a closed sieve was filled with sample. After opening the sieve, the sample flows from a height of 6.5 cm onto a 3 cm-radius metal cylinder placed below the sieve, building a powder cone. The height of the powder cone is measured and the angle of repose is calculated using the following formula:

Tan(x)=height of the powder cone/radius of the cylinder.

Figure 1:
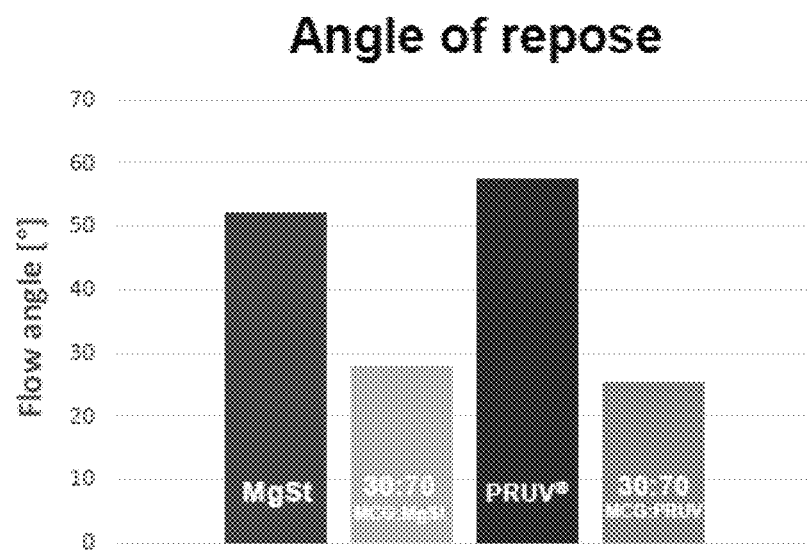
FIG. 1 graphically shows the Angle of repose results for Examples 2A and 2B, as compared to plain lubricant (Pruv® and magnesium stearate, respectively)

FIG. 1 provides a graphical representation of the Angle of repose results for Examples 2A and 2B, as compared to plain lubricant (Pruv® and magnesium stearate, respectively).

Figure 2:
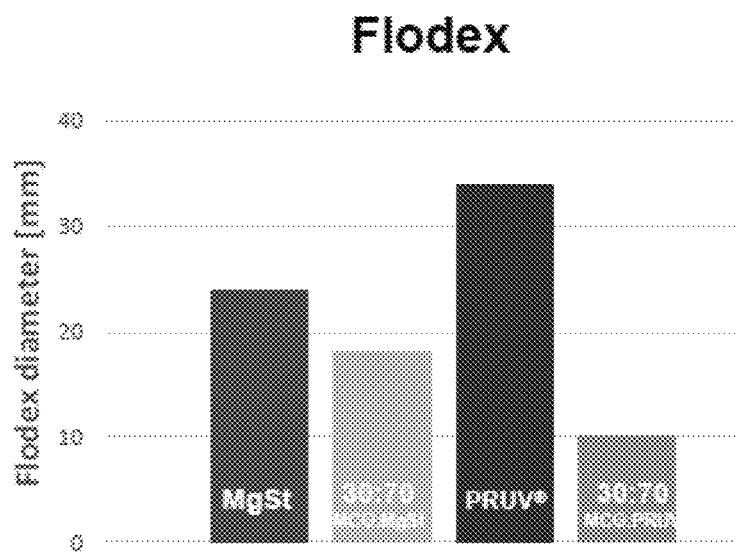
FIG. 2 graphically shows the Flodex diameter for Examples 2A and 2B, as compared to plain lubricant (Pruv® and magnesium stearate, respectively) graphically shows comparative compression profiles of the Prosolv Oil Excipient—Co-Processed (SD) versus Simple Blends (DC) of Example 2.

FIG. 2 provides a graphical representation of the Flodex diameter for Examples 2A and 2B, as compared to plain lubricant (Pruv® and magnesium stearate, respectively). A Hanson Research Flodex™ was used to examine material flowability. The minimum aperture through which the powder flowed and the powder flow mass and time were recorded for each sample. 50 g of the powder were placed in the Flodex™ cup. The material was allowed to stand for 30 seconds before evaluation.

FIG. 3 provides a graphical representation of the Bulk Density for Examples 2A and 2B, as compared to plain lubricant (Pruv® and magnesium stearate, respectively). A Scott Volumeter was used to determine the bulk density. The samples were poured through the funnel (screen in place) and baffle box into a 100.00 ml brass cylindrical cup to overflowing. The excess material was scraped off flush with the cup rim. The weight in the cup was determined using the difference in mass between the empty cup and the cup filled with sample. The density was calculated using this mass and the cup volume.

$$\rho_b = \frac{m}{v}$$

As shown in FIGS. 1-3, the co-processing of MCG with the lubricant significantly improves the flowability of the lubricant as compared to the plain lubricant (as demonstrated by the decrease in the Angle of repose in FIG. 1, and the decrease in Flodex diameter in FIG. 2). Further, the co-processing of MCG with the lubricant significantly improves the Bulk Density of the lubricant as compared to the plain lubricant (as demonstrated by the increase in the Bulk Density in FIG. 3).

EXAMPLE 3—FUNCTIONALITY STUDIES

In Example 3A, a co-processed excipient consisting of 30:70 VIVAPUR® MCG:PRUV® is prepared and is then incorporated into an MCC-based formulation of VIVAPUR® 102. The present invention (co-processed lubricant) was dry blended with the microcrystalline cellulose (VIVAPUR® 102) for three minutes to a homogeneous mixture and the mixture was subsequently tableted on a rotary tablet press. Control tablets were made in similar fashion with plain PRUV®.

The amount of pure lubricant was kept at 1.5% in each formulation with VIVAPUR® 102 to reproduce the typical amount of lubricant present in pharmaceutical formulations (approximately the middle of the range).

To keep the lubricant amount at 1.5% for each formulation, more co-processed spray-dried lubricant (%) was added to the formulation, compared to plain lubricant, to keep the lubricant-proportion, and thus the lubricant effect, constant in the formulation, as follows:

| VIVAPUR® Formulation with plain lubricant | |
|---|---|
| VIVAPUR® 102 | 98.5% |
| Lubricant (MgSt or PRUV®) | 1.5% |
| VIVAPUR® Formulation with co-processed spray-dired lubricant | |
| VIVAPUR® 102 | 97.86% |
| Spray-dried Lubricant (MgSt or PRUV®: MGC, 70:30) | 2.14%* |

*70% of 2.14% corresponds to 1.5% of pure lubricant in the formulation

In Example 3B, a co-processed excipient formulation consisting of 30:70 VIVAPUR® MCG:Magnesium stearate is prepared and is then incorporated into an MCC-based formulation of VIVAPUR® 102. The present invention (co-processed lubricant) was dry blended with the microcrystalline cellulose (VIVAPUR® 102) for three minutes to a homogeneous mixture and the mixture was subsequently tableted on a rotary tablet press. Control tablets were made in similar fashion with plain magnesium stearate. Three minutes is considered the standard blending time to ensure a homogenous mixture. Upon higher blending times (beyond 3 minutes) the lubricant (especially the magnesium stearate) might get overblended, compromising the tablet hardness of the produced tablets. Therefore, the comparison on tablet hardness was carried out after 3 minutes blending time. That means that the higher tablet hardness achieved with the present invention (co-processed spray-dried lubricant) corresponds to the hardness achieved after a "standard" blending time.

The crushing strength [N] and the compression force [kN] of the tablets were measured. FIG. 4 is a graph plotting crushing strength against compression force for tablets containing 30:70 VIVAPUR® MCG:PRUV® and tablets containing plain PRUV®.

The crushing strength [N] and the compression force [kN] of the tablets were measured. Immediately following compression, ten tablets produced with each compression force were analyzed regarding tablet hardness using the tablet hardness tester. Any of the ten randomly selected tablets was placed in a chamber of the feeder and was then transported automatically to the measuring station where the tablet's thickness, diameter, and crushing force were measured. FIG. 5 is a graph plotting crushing strength against compression force for tablets containing 30:70 VIVAPUR® MCG:magnesium stearate and tablets containing plain magnesium stearate.

As can be seen from the results provided in FIGS. 4 and 5, the co-processed excipient formulation increases the hardness of the resulting tablets, as compared to tablets made using the plain lubricant.

The disintegration time (minutes) was also measured for the tablets made in Example 3. 24 hours after compression, disintegration time of six randomly selected tablets of each compression force was measured according to Ph. Eur. 2.9.1., with automatic end-point detection. The test medium was demineralized water with a temperature of 37±1° C. The disintegration time [minutes] was plotted against the crushing strength [N] in FIG. 6 for tablets containing 30:70 VIVAPUR® MCG:PRUV® and tablets containing plain PRUV®.

The disintegration time [minutes] was plotted against the crushing strength [N] in FIG. 7 for tablets containing 30:70 VIVAPUR® MCG:magnesium stearate and tablets containing plain magnesium stearate.

As can be seen from the results provided in FIGS. 6 and 7, the formulations with the co-processed excipient of the invention (co-processed lubricant) present comparable disintegration times as compared to the tablet formulations with plain lubricant, even though the tablets using the co-processed lubricants are harder.

EXAMPLE 4

A multifunctional, co-processed excipient comprising (i) microcrystalline cellulose, (ii) colloidal silicone dioxide, (iii) magnesium stearate, (iv) croscarmellose sodium or sodium starch glycolate and (v) carmellose sodium is prepared.

First, an aqueous suspension of the co-processed excipient formulation of the present invention is prepared. The suspension is then sprayed onto a fluidized bed comprising a blend of microcrystalline cellulose, colloidal silicone dioxide, and croscarmellose sodium or sodium starch glycolate.

The obtained multifunctional, co-processed excipient may then be used in the preparation of solid dosage forms. For example, the multifunctional, co-processed excipient may be compressed into a tablet with or without one or more active pharmaceutical ingredient(s) and with or without additional tableting excipients. The co-processed excipient may also be incorporated into a capsule, along with additional excipients with or without one or more active pharmaceutical ingredient(s).

Conclusion

All of the percentages in the specification and specifically in the Examples provided above are expressed as w/w unless otherwise indicated.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. An excipient composition, consisting of agglomerated particles of microcrystalline cellulose, a cellulose ether, and a pharmaceutically acceptable lubricant, wherein the agglomerated particles consist of about 24 to about 28% microcrystalline cellulose, from about 3 to about 6% cellulose ether, and from about 60 to about 80% pharmaceutically acceptable lubricant.

2. The excipient composition of claim 1, wherein the microcrystalline cellulose and the cellulose ether are co-processed prior to being co-processed with the pharmaceutically acceptable lubricant.

3. The excipient composition of claim 1, wherein the microcrystalline cellulose, cellulose ether and pharmaceutically acceptable lubricant are co-processed by a process comprising spray-drying.

4. The excipient composition of claim 2, wherein the microcrystalline cellulose and cellulose ether are in the form of agglomerated particles containing the microcrystalline cellulose and cellulose ether prior to co-processing with the pharmaceutically acceptable lubricant.

5. The excipient composition of claim 1, wherein the cellulose ether is an alkali metal cellulose ether.

6. The excipient composition of claim 5, wherein the alkali metal cellulose ether is sodium carboxymethylcellulose.

7. The excipient composition of claim 6, wherein the pharmaceutically acceptable lubricant is selected from the group consisting of earth alkaline stearates, alkali stearyl fumarate, stearic acid and its salts, or mixtures thereof.

8. The excipient composition of claim 5, wherein the pharmaceutically acceptable lubricant is magnesium stearate.

9. The excipient composition of claim 5, wherein the pharmaceutically acceptable lubricant is sodium stearyl fumarate.

10. The excipient composition of claim 2, wherein the ratio of microcrystalline cellulose to cellulose ether prior to co-processing with the lubricant is from about 11.3% to about 18.8% cellulose ether, and from about 81.2% to about 88.7% microcrystalline cellulose.

11. The excipient composition of claim 10, wherein the ratio of the pharmaceutically acceptable lubricant to the combination of microcrystalline cellulose and cellulose ether is from about 40:60 to about 90:10.

12. The excipient composition of claim 2, wherein the ratio of the pharmaceutically acceptable lubricant to the combination of microcrystalline cellulose and cellulose ether is about 70:30.

13. The excipient composition of claim 1, which comprises agglomerated particles of from about 8 to about 55% microcrystalline cellulose, from about 1 to about 12% cellulose ether, and from about 40 to about 90% pharmaceutically acceptable lubricant.

14. A pharmaceutical solid dosage form, consisting of an excipient composition comprising pre-agglomerated particles of a co-processed excipient of 24 to about 28% microcrystalline cellulose, from about 3 to about 6% of a pharmaceutically acceptable cellulose ether, and from about 60 to about 80% of a pharmaceutically acceptable lubricant; an active ingredient; and optional pharmaceutical excipients.

15. The pharmaceutical solid dosage form of claim 14, wherein the optional pharmaceutical excipients are selected from the group consisting of diluents, plasticizers, lubricants, binders, granulating aids, colorants, flavorants, glidants, sustained or delayed release carriers, and combinations of any of the foregoing.

16. The pharmaceutical solid dosage form of claim 15, wherein the cellulose ether is sodium carboxymethylcellulose and the pharmaceutically acceptable lubricant is selected from the group consisting of magnesium stearate, sodium stearyl fumarate, and mixtures thereof.

17. The pharmaceutical solid dosage form of claim 15 wherein the ingredients are compressed into tablets or filled into capsules.

18. An aqueous suspension consisting of a microcrystalline cellulose, a cellulose ether, and a pharmaceutically acceptable lubricant in an aqueous solvent.

19. The aqueous suspension of claim 18, wherein the microcrystalline and cellulose ether are previously co-processed prior to incorporation of the pharmaceutically acceptable lubricant, the ratio of microcrystalline cellulose/cellulose ether to the pharmaceutically acceptable lubricant is from about 60:40 to about 10:90, and water content is from about 85% to about 98% of the suspension.

20. The aqueous suspension of claim 19, wherein the amount of microcrystalline cellulose/cellulose ether in the suspension is from about 1% to about 5% of the suspension, and the amount of pharmaceutically acceptable lubricant is from about 1 to about 15% of the suspension.

21. The aqueous suspension of claim 20, wherein the amount of microcrystalline cellulose/cellulose ether in the suspension is about 1.5% and the amount of pharmaceutically acceptable lubricant is about 3.5%.

22. The aqueous suspension of claim 21, wherein the microcrystalline cellulose and cellulose ether are co-processed to provide agglomerated excipient particles prior to incorporation into the aqueous suspension.

23. The aqueous suspension of claim 21, wherein the resultant solid agglomerated particles are mixed with an active ingredient and optional excipients and compressed into a tablet or filled into capsules.

* * * * *